(12) United States Patent
Tanaka et al.

(10) Patent No.: US 6,441,073 B1
(45) Date of Patent: Aug. 27, 2002

(54) BIOLOGICAL MATERIALS

(75) Inventors: Junzo Tanaka; Masanori Kikuchi, both of Tsukuba; Kimihiro Miyamoto, Saiki; Shuji Suwa, Yokohama; Shunji Ichikawa, Ohno-gun; Etsuro Yokoyama, Funabashi; Soichi Shono, Akashi; Takao Okada, Kakogawa; Yukari Imamura, Himeji; Kazuo Takakuda, Nerima-ku; Yoshihisa Koyama, Kawasaki; Shigeo Tanaka, Musashino; Noriaki Shirahama; Takatoshi Itoh, both of Ohno-gun, all of (JP)

(73) Assignees: Taki Chemical Co., Ltd. (JP); National Institute for Material Science President (JP)

( * ) Notice: Subject to any disclaimer, the term of this patent is extended or adjusted under 35 U.S.C. 154(b) by 0 days.

(21) Appl. No.: 09/807,707

(22) PCT Filed: Aug. 10, 2000

(86) PCT No.: PCT/JP00/05353

§ 371 (c)(1),
(2), (4) Date: Apr. 17, 2001

(87) PCT Pub. No.: WO01/12240

PCT Pub. Date: Feb. 22, 2001

(30) Foreign Application Priority Data

Aug. 17, 1999 (JP) .......................... 11-230348
Jan. 11, 2000 (JP) ........................ 2000-002240
Jun. 21, 2000 (JP) ........................ 2000-185878

(51) Int. Cl.$^7$ ..................... C08K 3/32; C08L 67/04; C08G 63/08; A61F 2/28
(52) U.S. Cl. ................. 524/414; 524/599; 523/113; 523/115; 528/302; 424/426
(58) Field of Search ................. 524/414; 523/113, 523/115; 424/426; 528/302

(56) References Cited

U.S. PATENT DOCUMENTS

| | | | |
|---|---|---|---|
| 4,347,234 A | 8/1982 | Wahlig et al. | 424/15 |
| 4,595,713 A | 6/1986 | St. John | 523/105 |
| 4,603,695 A | 8/1986 | Ikada et al. | 128/334 R |
| 5,747,390 A | 5/1998 | Cooper et al. | 422/59 |
| 6,303,697 B1 * | 10/2001 | Yuan et al. | |

FOREIGN PATENT DOCUMENTS

| | | |
|---|---|---|
| JP | 60-14861 | 1/1985 |
| JP | 3-295561 | 12/1991 |
| JP | 6-298639 | 10/1994 |
| JP | 9-132638 | 5/1997 |
| JP | 10-324641 | 12/1998 |
| JP | 11-192299 | 7/1999 |

\* cited by examiner

*Primary Examiner*—Tae H. Yoon
(74) *Attorney, Agent, or Firm*—Kennedy Covington Lobdell & Hickman, LLP

(57) ABSTRACT

The followings are disclosed herein:
a biomaterial comprising calcium phosphate and a copolymer of lactic acid, glycolic acid and ε-caprolactone;
a biomaterial for the induction of osteoanagenesis, characterized in that a periosteum is attached to the biomaterial comprising calcium phosphate and a copolymer of lactic acid, glycolic acid and ε-caprolactone; and a biomaterial for the prevention of adhesion comprising calcium phosphate and a copolymer of lactic acid, glycolic acid and ε-caprolactone where the molar ratio of lactic acid, glycolic acid and ε-caprolactone is within a range of 5–90:3–75:5–40.

14 Claims, No Drawings

BIOLOGICAL MATERIALS

BACKGROUND OF THE INVENTION

1. Field of the Invention

The present invention relates to a biomaterial comprising calcium phosphate and a copolymer of lactic acid, glycolic acid and ε-caprolactone and, more particularly, it relates to an excellent material for organism which is applied to reconstruction of hard tissues and soft tissues in vivo and is gradually degraded and absorbed together with the tissue formation. The present invention further relates to a biomaterial for the induction of osteoanagenesis where periosteum is provided to the above biomaterial by means of suture or adhesion and, particularly, to a biomaterial for the induction of osteoanagenesis which is applied as a quick therapy of big bone defect and is gradually degraded and absorbed. The present invention furthermore relates to a biomaterial for the prevention of adhesion which is applied for the prevention of adhesion of the tissues produced as a result of a self-repair after an operation or by damage of tissues of organism and is gradually degraded and absorbed.

2. Description of the Related Art

Defected area in organism which is caused by injury, inflammation, tumor excision or reconstructive cosmetology of hard tissues such as bone tissue and cartilaginous tissue and soft tissues such as epithelial tissue, connective tissue and nervous tissue has already been subjected to a prosthetic treatment and to a functional recovery by various methods and there have been also many studies for the materials used therefor.

In subjecting the bone defect area in organism to a prosthetic treatment, a self bone implantation showing abetter take to implanted area and having less infection of virus, prion, etc. or less immunological problem than homoimplantation and heteroimplantation has been carried out already. However, in the case of the self bone implantation, there is a limitation in a collectable amount and, in addition, there are problems such as a risk for infection by formation of new surgical wound for obtaining the bone to be implanted and a tendency that pain of the patient becomes longer.

As a substitute for a self bone implantation, there is a method where metal materials such as stainless steel and titanium alloy are used as artificial biomaterials and, because of a significant progress of biomaterials and an easy availability of the materials, they have been used actually.

However, in those biomaterials, their physical and mechanical strength is much more than that of tissues of organism and there is a toxicity of the metal contained therein due to corrosion. In addition, their affinity to organism is inferior as well.

Therefore, as a method for improving the affinity to organism, there has been conducted a method where the surface of the metal material is subjected to a surface treatment by a bioaffinitive material such as hydroxyapatite whereby its affinity to the surrounding tissues is improved but that is still insufficient.

On the other hand, as bioaffinitive materials, polymers of lactic acid, glycolic acid, trimethylene carbonate or lactone such as ε-caprolactone and copolymers thereof which are biodegradable aliphatic polyesters have been investigated as reparative materials as well and, in addition, a block copolymer of polylactic acid, poly-ε-caprolactone and polyglycolic acid as mentioned in Japanese Patent Laid-Open Hei-09/132638 has also been investigated. However, those materials lower their mechanical strength upon degradation in vivo resulting in a fatigue deterioration and, although bone conduction is not inhibited, they rarely show an action for bone induction.

On the other hand, bioceramics such as alumina, bioglass, A-W crystallized glass and hydroxyapatite have a high bioaffinity, have been utilized as materials for artificial bone, dental implant, etc. and noted of formation of new bone on the surface in organism and have excellent filling function and adhesion to bone tissues.

However, since those are the materials which are not absorbed in organism, there is a problem that they remain in the formed bone tissues and affect the growth of new bones and that strength of the bone lowers. Tricalcium phosphate is a material which is absorbed in vivo and, when it is used to a defected area of bone, it is absorbed or collapsed from the surface of the material and is substituted for the new bone, but its mechanical strength is weak as compared with the bone, its use to the area where load such as body weight is applied is limited.

In addition, tricalcium phosphate is in granules and, therefore, it has little ability of giving a shape to a bone implantation material and of maintaining/stabilizing thereof whereupon there is a problem that a filling operation is difficult to a complicated and broad defect and that cure is delayed due to flowing-out of the granules.

In order to solve such problems, many materials where bioceramics and polymers are compounded have been studied. In U.S. Pat. No. 4,347,234, a complex of bioceramics with collagen is proposed. However, when such collagen i s used, its molecular weight, amino acid composition, quantity, water-holding amount, etc. are not constant because it is a material derived from nature and, in addition, a complete removal of it causes a foreign body reaction in vivo and foreign body giant cell and other phagocytes, etc. are activated whereupon a bone induction is hardly expressed.

In place of collagen, there have been proposals for many materials where aliphatic polyesters such as polylactic acid having no problem in terms of immunology are compounded with hydroxyapatite. In Japanese Patent Laid-Open Hei-10/324641, there is disclosed an absorbable isolating membrane consisting of calcium phosphate and a lactic acid type polyester having a dicarboxylic acid and a diol where a polymerization catalyst is inactivated. In U.S. Pat. No. 4,595,713, there is disclosed a complex consisting of a osteoanagenetic substance such as calcium β-phosphate and hydroxyapatite and a copolymer of lactic acid with ε-caprolactone where ε-caprolactone occupies the most of the amount. The former is absorbable in vivo and has a bone induction property but, since a lactic acid segment and other components are blocked, property of calcium phosphate appears and properties of forming, retaining and stabilizing the shape are little. In the latter, its mechanical strength to the applied tissue is low and a degradation rate of the material is slow whereby osteoanagenesis is suppressed. In any of the materials, the problem of little osteoanagenetic amount of calcium β-phosphate in vivo is not solved.

In Japanese Patent Laid-Open Hei-06/298639, there is disclosed a sustained-released material where tricalcium β-phosphate is dispersed in a complex of an antibiotic substance with a lactic acid/glycolic acid copolymer.

Although there have been many other studies concerning reconstruction of soft tissues such as blood vessel and peripheral nerve, a sufficient material has not been available and, accordingly, there has been a demand for a material having a metabolism similar to that of tissues where a biocompatibility is excellent, strength can be maintained until the tissues are regenerated and degradation and absorption take place after the implantation.

With regard to a biomaterial for induction of osteoanagenesis, a sole use of a material has a limitation for the therapeutic effect and, therefore, with an object of supplementing the osteoanagenetic amount, there have been many studies for a substitution therapy where filling of bone marrow is utilized. Since bone marrow has many osteoanagenetic cells, its bone inducing property is high. However, with regard to the use of bone marrow, there is a limitation in the collecting amount thereof. In addition, its application is complicated and, to a defect in a broad area, a filling operation is difficult and there has been no satisfactory material in terms of a shape-giving property and a retention-stabilizing property. for the prevention of flowing out.

On the other hand, with regard to a material having an osteoanagenetic ability like bone marrow, there is a periosteum where osteoblasts are abundantly present. As compared with bone marrow, periosteum can be easily collected in large quantities as a membrane without leaving a surgical wound and there is no invasion in the bone wherefrom it is collected because it is regenerated even if taken out. In addition, periosteum is a tough membrane and, therefore, there is no problem such as flowing-out at bone marrow.

As such, it has been expected to conduct a treatment of a big bone defect area by application of periosteum and a material having an osteoanagenetic property but it is a current status that no osteoanagenetic material having a sufficient property for retaining and stabilizing the periosteum in a filmy form has been available.

Now, biomaterials for the prevention of adhesion will be discussed. A tissue adhesion which is a physiological action after orthopedic, cerebral, thoracic and abdominal surgical operations is due to an adhesion of the organs with the surrounding tissues caused by the production of collagen fiber by fibroblasts as a result of damage of the tissue. Generation of complications accompanied by such an adhesion or adhesion of the nerve with the area where scarred tissue is formed causes pain, biofunction disturbance, etc. and, therefore, that is a problem to a patient due to psychic and physical pain.

With regard t o such a problem, various methods and many materials used therefor have been studied already. For example, prevention of the adhesion by means of administration of a pharmacological agent such as antithrombotic agent or application of a hyaluronic acid solution or a copolymer of ethylene oxide and propylene oxide is available but, although such a method has a temporary adhesion-preventing action, there is a disadvantage that it is apt to flow out and does not have a sustained effect.

For a physical separation of biotissues, there has been carried out a method where silicon, Teflon, polyurethane, oxidized cellulose, or the like is used as a film for the prevention of adhesion. However, they are non-absorbable materials and, therefore, they remain on the surface of the biotissues, which results in not only a delay in repair of the tissues but also a cause of infection and inflammation.

As a means for solving such a problem, Japanese Patent Laid-Open Hei-03/295561 proposes a film where collagen is a main component. In addition, cattle pericardium and horse pericardium which are cross-linked with glutaraldehyde are available. However, when such a collagen is used, a complete removal of a telopeptide moiety having antigenicity is difficult and there is a risk of contamination of prion or the like since collagen is a material derived from nature. Further, an aldehyde or an isocyanate is used as a cross-linking agent for controlling the degradation of the adhesion-preventing film but, in the use of such an agent, the degraded product shows a bad affection in vivo and that is not preferred.

In Japanese Patent Laid-Open Sho-60/14861, in place of collagen, there is proposed an adhesion-preventing material consisting of a biodegradable/bioabsorbable high-molecular material such as a copolymer of lactic acid with glycolic acid or a copolymer of lactic acid with caprolactone having no problem in terms of immunology. In Japanese Patent Laid-Open Hei-11/192299, there is disclosed a complex material consisting of a biologically active ceramics and a copolymer comprising a combination of p-dioxanone, lactic acid, trimethylene carbonate and caprolactone.

When the inside of the organism changes to a circumstance where adhesion of tissue takes place, tissues become very adhesive to each other and, therefore, a mechanical strength is required because it is necessary to keep the effect of preventing the adhesion for 1–2.5 months and the adhesion-preventing material is held to the tissue by means of suture. However, those materials are insufficient in terms of both degradation and strength retention.

Although there have been many studies for the prevention of adhesion of tissues as such, no material having a sufficient property as a material for the prevention of adhesion has been available and it is the current status that there has been a demand for a soft material which has an excellent biocompatibility, does not cause an immune reaction such as flare, swelling and induration at the site where the adhesion-preventing material is applied, prevents the adhesion during the period until the tissues are repaired and is degraded and absorbed within a short period after the tissues are repaired.

In order to solve the above-mentioned problems, the present inventors have carried out an intensive study for a biomaterial which has a biodegradability, does not produce a foreign body reaction in vivo, has appropriate strength and degradability and is effective for the regeneration of tissues.

The present inventors have further carried out an intensive study for a biomaterial having an appropriate softness for retention and stabilization of periosteum as an osteoanagenesis inducing material and also for a biomaterial for induction of osteoanagenesis produced by attaching periosteum thereto.

The present inventors have furthermore carried out an intensive study for a biomaterial for the prevention of adhesion which has a biodegradability, does not produce a foreign body reaction in vivo, has appropriate strength and degradability and does not inhibit the repair of the tissues as an adhesion-preventing material.

As a result, the present invention which will be mentioned in detail as hereunder has been accomplished.

SUMMARY OF THE INVENTION

Thus the present invention relates to a biomaterial comprising calcium phosphate and a copolymer of lactic acid, glycolic acid and ε-caprolactone.

The present invention further relates to a biomaterial for the induction of osteoanagenesis where periosteum is attached by means of suture or adhesion to a biomaterial comprising calcium phosphate and a copolymer of lactic acid, glycolic acid and ε-caprolactone where the molar ratio of lactic acid, glycolic acid and ε-caprolactone is within a range of 5–90:3–75:5–40 molar %.

The present invention still further relates to a biomaterial for the prevention of adhesion comprising calcium phosphate and a copolymer of lactic acid, glycolic acid and ε-caprolactone where the molar ratio of lactic acid, glycolic acid and ε-caprolactone is within a range of 5–90:3–75:5–40 molar %.

DETAILED DESCRIPTION OF THE PREFERRED EMBODIMENTS

Now the present invention will be illustrated in more detail as hereinafter.

The copolymer of lactic acid, glycolic acid and ε-caprolactone used in the present invention may be that which is prepared by any method so far as it is manufactured by common means. An example for the manufacture is that lactide, glycolide and ε-caprolactone are heated in the presence of a catalyst such as stannous octoate, tin chloride, dibutyl tin dilaurate, aluminum isopropoxide, titanium tetraisopropoxide and triethyl zinc to carry out a ring-opening polymerization at 100° C. to 250° C. Monomer of the lactic acid and the lactide used for the polymerization may be any of D-, L- and DL-compounds or may be a mixture thereof. When monomer and oligomer are present in the resulting copolymer, tissue reaction and degradation rate are abnormally accelerated and degraded segments are produced in the absorbing/degrading ability more than that of macrophage, whereby the tissue degeneration is caused. Accordingly, it is preferred to use after being purified by, for example, means of reprecipitation.

The copolymer of lactic acid, glycolic acid and ε-caprolactone varies in its mechanical strength, softness and hydrolyzing rate depending upon the composition and the molecular weight and, with regard to the copolymer used in the present invention, it is preferred that the ε-caprolactone content therein is 1–45 molar %. When the content of ε-caprolactone is less than 1 molar %, the copolymer has a high rigidity and is fragile and, therefore, it cannot be applied because the close adhesion to the biotissues lowers and the degradation rate becomes slow. On the contrary, when the content is more than 45 molar %, the necessary strength is not achieved and, in addition, the biodegradability and bioabsorbability become slow and that is not preferred.

The lactic acid content and the glycol acid content in the copolymer can be freely changed but, when the glycolic acid content is less than 5 molar %, there are problems that the necessary degradation rate is not achieved and that regeneration of the tissues is inhibited while, when it is more than 70 molar %, tissue degeneration may be resulted due to the above-mentioned degraded segments.

The biomaterial of the present invention is in such a structure that calcium phosphate is coordinated by a carbonyl group of the copolymer of lactic acid, glycolic acid and ε-caprolactone and, therefore, biodegradability and biotissue inducing ability of calcium phosphate are adjusted whereby its biotissue inducing ability can be significantly promoted. Generally, the shape of the reconstructed biotissue is complicated but, when the composition and the molecular weight of the copolymer of lactic acid/glycolic acid/ε-caprolactone are adjusted, various types of material ranging from flexible ones to highly strong ones are formed and, accordingly, the biomaterial of the present invention is not deformed by compression of the tissue but is able to be fixed in a tightly closed manner to the tissue. In addition, it is possible to adjust to the degradation rate which is adaptable to the wound of the site to be applied and, therefore, regeneration of the biotissue is not inhibited but a quick tissue repair is possible.

Thus, when the biomaterial of the present invention is used as a reconstructing material for hard and soft tissues in vivo, it is quickly and directly bonded to the tissue, retains its strength during the period until the tissue is regenerated and is gradually absorbed into the organism together with the formation of the new biotissue and, accordingly, it is a biocompatible material which is able to be applied to a broad area.

As hereunder, the biomaterial for the induction of osteoanagenesis according to the present invention will be mentioned in detail.

With regard to the periosteum used in the present invention, a self-periosteum is preferred and, in the case of such a self-periosteum, it is possible to use after collecting from all sites of the organism wherefrom periosteum can be collected. For example, when the periosteum excised by a primary surgical operation in the therapy of bone defect site is used, it is easily available in large quantities. The periosteum which is collected before the operation and is preserved can be used as well. The above-mentioned periosteum is that which is derived from organism but, if an artificial periosteum having the substantially same function as the above-mentioned periosteum derived from organism will be developed in future, such an artificial periosteum may be used as well.

Attachment of the periosteum to the biomaterial may be carried out by any means so far as the periosteum can be fixed and its examples are a suture by means of an absorbable suture and an adhesion by means of a fibrin adhesive. The form of the attachment of the periosteum to the biomaterial may be freely designed depending upon the form (fiber, film, block, tube, etc.) of the biomaterial. For example, the periosteum may be attached to all of or a part of the surface (one side, both sides, inner surface or outer surface) of the biomaterial depending upon the object of the therapy.

The preferred form of the osteoanagenesis inducing material according to the present invention is a filmy shape where periosteum is attached by the above-mentioned means to the surface of the biomaterial in a filmy form and is made round into a tubular form so that the periosteum is contacted to the bone defect site.

It is preferred that the rigidity of the osteoanagenesis inducing material of the present invention is adjusted to 200–20000 MPa at 4–40° C. When it is less than 200 MPa, the rigidity is low and is too soft to apply to the filmy shape while, when it is more than 20000 MPa, the rigidity is high and is too hard to apply to the filmy shape whereby it is impossible to attach the periosteum to the defect site.

Method for the manufacture of the copolymer of lactic acid, glycolic acid and ε-caprolactone used in the present invention is as mentioned already.

With regard to the copolymer which is used as the material for the induction of osteoanagenesis of the present invention, a copolymer of lactic acid, glycolic acid and ε-caprolactone where the molar ratio of lactic acid, glycolic acid and ε-caprolactone is within a range of 5–90:3–75:5–40 molar % preferred.

Here, when the content of ε-caprolactone is less than 5 molar %, the copolymer has a high rigidity and is fragile whereby attachment of the periosteum thereto is difficult and there is possibility that the biotissue is damaged by the polymer segments. On the other hand, when it is more than 40 molar %, the necessary strength is not achieved and, in addition, biodegradability and bioabsorbability become slow.

The contents of lactic acid and glycolic acid in the copolymer can be freely changed but, when the glycolic acid content is less than 3 molar %, there are problems that the necessary degradation rate is not achieved and that the tissue repair is disturbed while, when it is more than 75%, damage of the tissue may take place by the degraded segments mentioned above.

The lactic acid content in the copolymer is within a range of 5–90 molar % and, when the lactic acid content is less than 5 molar %, the necessary degradation rate is not achieved and repair of the bone tissue is inhibited while, when it is more than 90 molar %, the rigidity becomes high and there is, a possibility that the biotissue is damaged by the polymer segments.

Now, the biomaterial for the prevention of adhesion according to the present invention will be mentioned in detail.

Method for the manufacture of a copolymer of lactic acid, glycolic acid and ε-caprolactone used in the present invention is as mentioned above.

With regard to the copolymer which is used for the present invention, a copolymer of lactic acid, glycolic acid and ε-caprolactone where the molar ratio of lactic acid, glycolic acid and ε-caprolactone is within a range of 5–90:3–75:5–40 molar % is preferred.

Here, when the content of ε-caprolactone is less than 5 molar %, the copolymer has a high rigidity and is fragile whereby there is a possibility that the biotissue is damaged by the polymer segments. On the other hand, when it is more than 40 molar %, the necessary strength is not achieved and, in addition, biodegradability and bioabsorbability become slow.

The contents of lactic acid and glycolic acid in the copolymer can be freely changed but, when the glycolic acid content is less than 3 molar %, there are problems that the necessary degradation rate is not achieved and that the tissue repair is inhibited while, when it is more than 75%, damage of the tissue may take place by the degraded segments mentioned above.

The lactic acid content in the copolymer is within a range of 5–90 molar % and, when the lactic acid content is less than 5 molar %, the necessary degradation rate is not achieved and repair of the bone tissue is inhibited.

When it is more than 90 molar %, the rigidity becomes high and there is a risk that the biotissue is damaged by the polymer segments.

It is preferred that the number-average molecular weight of the copolymer of lactic acid, glycolic acid and ε-caprolactone is 30,000–200,000. When the molecular weight of the copolymer is out of the above range and is lower than 30,000, a lot of monomers and oligomers such as lactic acid and glycolic acid are contained and, therefore, there is a problem of strong stimulation to the biotissues and, in addition, hydrolysis is promoted resulting in a reduction in the strength whereby physical properties and adhesion-preventing effect during the necessary period are not available. On the other hand, when the molecular weight is more than 200,000, the hydrolyzing rate lowers inhibiting the repair of bone tissues and, in addition, a mixing operation with calcium phosphate is difficult whereby dispersion of calcium phosphate in the copolymer becomes non-homogeneous.

Incidentally, other copolymer components in small quantities may be contained as well within such an extent that the object of the present invention is not deteriorated. Examples of such copolymer components are β-hydroxybutyric acid and a cyclic monomer constituting a hydroxycarboxylic acid such as γ-butyrolactone and δ-valerolactone.

Examples of the calcium phosphate used in the present invention are tricalcium phosphate, hydroxyapatite and calcium secondary phosphate. The most preferred calcium phosphate in relation to the copolymer of the present invention is tricalcium phosphate which has a good affinity to the copolymer and is substituted with new tissues by absorption and disintegration in vivo promoting the regeneration and the repair of bone tissues. It is preferred to use calcium phosphate having an average particle size of 0.1 to 200 μm. When the average particle size is less than 0.1 μm, the dissolving rate is too quick to show a sufficient tissue-reconstructing ability and, in addition, degradation of the material is promoted whereby sufficient effects of bone repair and adhesion prevention are not achieved. On the contrary, when the average particle size is more than 200 μm, the dissolving rate becomes slow whereby the tissue reconstruction is inhibited and, in addition, the tissue repair is delayed due to calcium phosphate existing on the surface of the material. Further, the preferred tricalcium phosphate in the present invention is tricalcium phosphate which is sintered at 650–1500° C. As a result of the sintering, structure of tricalcium phosphate is stabilized resulting in a high density and, when the sintering temperature is lower than 650° C., an unstable structure where hydrated water is present in tricalcium phosphate is resulted whereby degradation of the polymer is promoted upon compounding. On the contrary, when it is higher than 1500° C., tricalcium phosphate begins to decompose and the components which inhibit biotissue reconstruction, bone tissue repair and biotissue repair are produced.

In order to prepare a biomaterial which has appropriate strength and degradation property and which is effective for the tissue regeneration, an osteoanagenetic induction material which is effective for the bone tissue repair and a material for the prevention of adhesion in the present invention, it is necessary to prepare a biomaterial, that is a complex of calcium phosphate with a copolymer of lactic acid, glycolic acid and ε-caprolactone. Such a complex or a biomaterial can be manufactured, for example, by the following method.

Thus, it is manufactured by heating and kneading calcium phosphate with a copolymer of lactic acid, glycolic acid and ε-caprolactone at the temperature of higher than the softening point of the copolymer. Although the condition of heating and kneading cannot be specified because it varies depending upon, for example, the composition and the molecular weight of the copolymer of lactic acid, glycolic acid and ε-caprolactone used and also upon the type and the physical property of calcium phosphate, it is preferably carried out in vacuo, in air or in a nitrogen atmosphere at 50–250° C. With regard to the kneading time, about 5–60 minutes are required. Examples of the methods for the manufacture of the biomaterial other than the heating/kneading method are a method where calcium phosphate is mixed with a copolymer of lactic acid, glycolic acid and ε-caprolactone in a solvent followed by removing the solvent and a method where they are subjected to a solid mixing followed by being subjected to a pressurized press or to a heating press.

Calcium phosphate and a copolymer of lactic acid, glycolic acid and ε-caprolactone may be mixed in any ratio and the resulting complex varies in its physical property such as tensile strength and degradation rate depending upon the mixing ratio. In general, however, it is preferred that the mixing ratio of calcium phosphate to the copolymer of lactic acid, glycolic acid and ε-caprolactone in terms of weight is 1:0.1~2.0. When the content of the copolymer of lactic acid, glycolic acid and ε-caprolactone is less than 0.1, the complex becomes fragile and lowers its shape-giving property and retention stability while, when the content of the copolymer of lactic acid, glycolic acid and ε-caprolactone is more than 2.0, the necessary strength and rigidity are not achieved and the tissue inducing and regenerating ability and the functions as an osteoanagenesis inducing material and an adhesion preventing material are reduced.

It is also possible that pharmaceuticals such as physiological substances including anti-tumor agent, anti-cancer agent, anti-inflammatory agent, vitamins (for example, vitamin D of an activated type) and polypeptide (for example, a thyroid stimulating hormone) are added to the complex to give a sustained released function whereby the tissue regeneration and the bone tissue repair are promoted within such an extent that the characteristics of the biomaterial, osteoanagenetic inducing material and adhesion preventing material obtained by the present invention are not deteriorated. It is further possible that the biomaterial, the osteoanagenesis inducing material and the adhesion preventing material of the present invention are used as an adhesion preventing film, an artificial blood vessel, a nerve repair inducing pipe, etc.

The complex and the osteoanagenesis inducing material which are manufactured as such can be molded by known methods such as casting, injection molding, extrusion molding and hot press and may be used in any form such as fiber, film, block and tube. It is also possible to prepare a porous product by, for example, means of a freeze-drying from a solvent.

In addition, the biomaterial, the osteoanagenesis inducing material and the adhesion preventing material according to the present invention have characteristics that they can be easily deformed by heating by, for example, means of dipping in hot water whereby their filling into a complicated site to be treated can be carried out easily. During the period from embedding and filling into organism until regeneration and repair of the tissue, the complex and the biomaterial retain their form and strength even near the body temperature and are quite effective for the utilization even to the site where a load such as body weight is applied.

EXAMPLES

The present invention will be further illustrated by way of the following examples although the present invention is not limited thereto. Incidentally, % stands for that by weight in all cases unless otherwise mentioned.

Example 1

L-Lactide (220 g), 35 g of glycolide and 45 g of ε-caprolactone were subjected to a polymerization reaction in the presence of 0.01 g of stannous octoate in vacuo ($10^{-3}$ mmHg) at 150° C. for 24 hours. After the reaction, the product was purified by dissolving in chloroform followed by separating in methanol to give 185g of copolymer of lactic acid, glycolic acid and ε-caprolactone.

The number-average molecular weight of the copolymer prepared as such by means of a GPC was 120,000 and its composition by means of an H-NMR in terms of molar ratio of lactic acid, glycolic acid and ε-caprolactone was 80:15:5.

The above-prepared copolymer of lactic acid, glycolic acid and ε-caprolactone was heated and kneaded at 200° C. for 10 minutes with tricalcium β-phosphate of an average particle size of 1 μm sintered at 800° C. in a ratio of 30/70 by weight. According to the result of the strength test, the resulting complex had a uniform composition, showed a strength near the bone strength and had a bending strength of 70 MPa and a Young's modulus of 25 GPa. As a result of the cell incubation experiment, both of tricalcium phosphate and the copolymer of lactic acid, glycolic acid and ε-caprolactone used for the complex showed the characteristics to organisms prior to making into a complex.

Examples 2–9

Copolymers of lactic acid, glycolic acid and ε-caprolactone having varied compositions were synthesized and made into complexes by mixing with calcium phosphate having different physical property in the ratios as shown in Tables 1–2 whereupon biomaterials were manufactured. The results are shown in Tables 1–2. Incidentally, their number-average molecular weights were about 90,000–120,000.

TABLE 1

| | Composition of Copolymer (Molar Ratio) | | | Tricalcium β-Phosphate | | Composition of Complex (Ratio by Weight) | | Property of Biomaterial | |
|---|---|---|---|---|---|---|---|---|---|
| | | | | Average Particle | Sintered Temp. | Tricalcium β- | | Bending Strength | Young's Modulus |
| Ex | LA | GA | CL | Size (μm) | (° C.) | Phosphate | Copolymer | (MPa) | (GPa) |
| 2 | 68 | 18 | 14 | 1 | 800 | 70 | 30 | 55 | 20 |
| 3 | 70 | 25 | 5 | 1 | 800 | 50 | 50 | 40 | 3 |
| 4 | 75 | 20 | 5 | 1 | 1200 | 70 | 30 | 60 | 18 |
| 5 | 75 | 20 | 5 | 100 | 800 | 70 | 30 | 65 | 20 |
| 6 | 60 | 10 | 30 | 1 | 800 | 70 | 30 | 40 | 2 |

Note:
LA . . . L-Lactic Acid
GA . . . Glycolic Acid
CL . . . ε-Caprolactone

TABLE 2

| | Composition of Copolymer (Molar Ratio) | | | Calcium Phosphate Species (sintered temperature: 800° C.; average particle size: 1 μm) | Composition of Complex (Ratio by Weight) | | Property of Biomaterial | |
|---|---|---|---|---|---|---|---|---|
| | | | | | Calcium | | Bending | Young's |
| Ex | LA | GA | CL | | Phosphate | Copolymer | Strength (MPa) | Modulus (GPa) |
| 7 | 80 | 15 | 5 | Tricalcium α-Phosphate | 70 | 30 | 40 | 15 |
| 8 | 75 | 20 | 5 | Hydroxyapatite | 50 | 50 | 70 | 15 |
| 9 | 75 | 20 | 5 | Hydroxyapatite | 70 | 30 | 100 | 20 |

<Evaluation of Biotissue Inducing Ability>

The biomaterials manufactured in Examples 2–4 were made into a film having a thickness of about 200 μm using a hot press, sterilized with ethylene oxide and implanted to an artificial defect of mandible of a dog. As a result, the complex film disappeared within about 4 weeks and the defect part was reconstructed within about 12 weeks.

Comparative Example 1

A binary copolymer of lactic acid with glycolic acid (80:20) having a number-average molecular weight of 100,000 was synthesized by the same method as in Example 1. This was heated and kneaded at 200° C. for 10 minutes with tricalcium α-phosphate being sintered at 800° C. and having an average particle size of 1 μm in a ratio of 70/30 by weight whereupon a complex was synthesized.

The resulting complex had a high rigidity and was fragile and, accordingly, its molding was difficult or, in other words, its shape was unable to be retained.

Comparative Example 2

A binary copolymer of lactic acid with ε-caprolactone (70:30) having a number-molecular weight of 110,000 was synthesized in the same way as in Comparative Example 1 and a complex was synthesized by the same method as in Comparative Example 1. The complex was made into a film having a thickness of about 200 μm using a hot press, sterilized with ethylene oxide and implanted to an artificial defect of mandible of a dog. As a result of an observation for about 12 weeks, the degradation rate of the complex was slow and regeneration of the tissue was inhibited.

Example 10

Evaluation of Bone Tissue Inducing Ability

L-Lactide (220 g), 35 g of glycolide and 196 g of ε-caprolactone were subjected a polymerization reaction in the presence of 0.01 g of stannous octoate in vacuo ($10^{-3}$ mmHg) at 150° C. for 24 hours. After the reaction, the product was purified by dissolving in chloroform followed by separating in methanol to give 273 g of a copolymer of lactic acid, glycolic acid and ε-caprolactone.

A number-average molecular weight of the copolymer prepared as such by means of a GPC was 100,000 and its composition (molar ratio) by means of an H-NMR was lactic acid/glycolic acid/ε-caprolactone=65/8/27.

The resulting copolymer of lactic acid, glycolic acid and ε-caprolactone was heated and kneaded at 180° C. for 10 minutes with tricalcium β-phosphate being sintered at 800° C. and having an average particle size of 10 μm in the ratio as shown in Table 3 whereupon a complex was prepared.

The biomaterial prepared as such was molded by a hot press method to manufacture a film having a thickness of 200 μm followed by sterilizing with ethylene oxide. Result of the physical property is shown in Table 3.

Result of the cell incubation test was that both of the tricalcium phosphate and the copolymer of lactic acid, glycolic acid and ε-caprolactone used as the above-mentioned filmy biomaterials retained their characteristics to organism before making into the complex.

An evaluation was carried out using an artificially deficient animal model where tibia of a dog was deficient in 20 mm. Periosteum collected from the defect part was sutured on the surface of the above-mentioned filmy biomaterial to prepare a filmy osteoanagenesis inducing material, the resulting osteoanagenesis inducing material was made round in a tubular shape so as to contact to the bone defect site and, at the same time, implanted by an absorbable suture so as to cover the defect part followed by fixing using an external skeletal fixer and then the elapse of the osteoanagenesis was observed by means of X-ray or the like.

As a result, disappearance of the osteoanagenesis inducing material after 4 weeks from the implantation and an early induction of regeneration of the bone at the defect site were observed by an observation of X-ray picture. After 8 weeks from the implantation, the animal was able to walk even when a wire of the external skeletal fixer was partially cut. After 12 weeks, an incision was conducted and disappearance of the osteoanagenesis inducing material and regeneration of the bone defect part were confirmed by naked eye. After 24 weeks, the animal was completely able to walk in such a state that the external skeletal fixer was removed.

Comparative Example 3

In accordance with the same method as in Example 10, a binary polymer of lactic acid and glycolic acid (80:20) having a number-average molecular weight of 100,000 was synthesized. This was heated and kneaded at 200° C. for 10 minutes with tricalcium α-phosphate being sintered at 800° C. and having an average particle size of 1 μm in a ratio of 70/30 by weight whereupon a complex was synthesized.

Since the resulting complex had a high rigidity and was fragile, its molding was difficult and the attaching the periosteum thereto using an absorbable suture was impossible either.

Comparative Example 4

In accordance with the same method as in Comparative Example 3, a binary copolymer of lactic acid and ε-caprolactone (70:30) having a number-average molecular weight of 110,000 was synthesized and then a complex was synthesized by the same method as in Comparative Example 3. The complex was made into a film having a thickness of about 200 μm using a hot press and sterilized with ethylene oxide, periosteum was attached thereto using an absorbable suture and the product was implanted to a bone defect part of tibia of a dog. After 12 weeks, an incision was conducted

TABLE 3

| Ex | Composition of Copolymer (Molar Ratio) | | | Calcium β-Phosphate | | Composition of Complex (Ratio by Weight) | | Physical Property of Complex Material (Room Temp) | |
|---|---|---|---|---|---|---|---|---|---|
| | | | | Average Particle Size(μm) | Sintered Temp. (° C.) | | | Tensile Strength (MPa) | Rigidity (MPa) |
| | LA | GA | CLT | | | Calcium β-Phosphate | Copolymer | | |
| 10 | 65 | 8 | 27 | 10 | 800 | 50 | 50 | 33 | 2300 | and an observation by naked eye revealed that the degradation rate of the complex was so slow that its residue was noted whereupon regeneration of the bone defect part was inhibited.

Example 11

L-Lactide (210 g), 35 g of glycolide and 53 g of ε-caprolactone were subjected to a polymerization reaction in vacuo ($10^{-3}$ mmHg) at 150° C. for 24 hours in the presence of 0.01 g of stannous octoate. After the reaction, the product was purified by dissolving in chloroform followed by separating in methanol whereupon 180 g of a copolymer of lactic acid, glycolic acid and ε-caprolactone were obtained.

The number-average molecular weight by means of a GPC of the copolymer prepared as such was 110,000 and the composition (in terms of molar ratio) by means of an H-NMR was lactic acid:glycolic acid:ε-caprolactone= 78:15:7.

The above-prepared copolymer of lactic acid, glycolic acid and ε-caprolactone was heated and kneaded at 200° C. for 10 minutes with tricalcium β-phosphate of an average particle size of 1 μm sintered at 800° C. in a ratio of 30/70 by weight. According to the result of the strength test, the resulting complex had a uniform composition and had a bending strength of 68 MPa and a Young's modulus of 25 GPa. As a result of the cell incubation experiment, both tricalcium phosphate and the copolymer of lactic acid, glycolic acid and ε-caprolactone used for the complex showed the characteristics to organisms as same as those prior to making into a complex.

Examples 12–17

Copolymers of lactic acid, glycolic acid and ε-caprolactone having varied compositions were synthesized and made into complexes by mixing with calcium phosphate having different physical property in the ratios as shown in Tables 4–5 where upon adhesion preventive materials were manufactured. The results are shown in Tables 4–5. Incidentally, the number-average molecular weights of the copolymers were about 90,000–120,000.

TABLE 4

| | Composition of Copolymer (Molar Ratio) | | | Tricalcium β-Phosphate | | Composition of Complex (Ratio by Weight) | | Property of Biomaterial | |
|---|---|---|---|---|---|---|---|---|---|
| | | | | Average Particle | Sintered Temp. | Tricalcium β- | | Bending Strength | Young's Modulus |
| Ex | LA | GA | CL | Size (μm) | (° C.) | Phosphate | Copolymer | (MPa) | (GPa) |
| 12 | 35 | 48 | 17 | 1 | 800 | 70 | 30 | 30 | 3 |
| 13 | 75 | 20 | 5 | 1 | 1200 | 70 | 30 | 60 | 18 |
| 14 | 75 | 20 | 5 | 100 | 800 | 70 | 30 | 65 | 20 |
| 15 | 62 | 7 | 31 | 1 | 800 | 70 | 30 | 50 | 5 |

Note:
LA . . . L-Lactic Acid
GA . . . Glycolic Acid
CL . . . ε-Caprolactone

TABLE 5

| | Composition of Copolymer (Molar Ratio) | | | Calcium Phosphate Species (sintered temperature: 800° C.; average particle size: 1 μm) | Composition of Complex (Ratio by Weight) | | Property of Biomaterial | |
|---|---|---|---|---|---|---|---|---|
| | | | | | Calcium | | Bending Strength | Young's Modulus |
| Ex | LA | GA | CL | | Phosphate | Copolymer | (MPa) | (GPa) |
| 16 | 78 | 15 | 7 | Tricalcium α-Phosphate | 70 | 30 | 38 | 15 |
| 17 | 50 | 45 | 5 | Hydroxyapatite | 50 | 50 | 40 | 7 |

<Evaluation of Adhesion Preventing Materials>

The adhesion preventing materials manufactured in Examples 11–17 were made into a film having a thickness of about 100 μm using a hot press and sterilized with ethylene oxide. A part (5×5 cm) of an intestinal tract of a dog (body weight: about 10 kg) was detached and the adhesion preventing material was fixed to the detached part by means of suture. Incisions were carried out after 4 weeks and 8 weeks and checking whether the detached part was adhered was carried out by naked eye and, as a result, in any of the adhesion preventing materials, the operated part was not adhered and repair of the tissue was noted.

Comparative Example 5

A binary copolymer of lactic acid with glycolic acid (70:30) having a number-average molecular weight of 100, 000 was synthesized by the same method as in Example 11. This was heated and kneaded at 200° C for 10 minutes with tricalcium α-phosphate being sintered at 800° C. and having an average particle size of 1 Am in a ratio of 70/30 by weight whereupon a complex was synthesized. The resulting complex was made into a film having a thickness of about 100 μm using a hot press but, since it had a high rigidity and was fragile, it was broken upon the stage of suture.

Comparative Example 6

A binary copolymer of lactic acid with ε-caprolactone (70:30) having a number-molecular weight of 110,000 was synthesized in the same way as in Comparative Example 5 and a complex was synthesized by the same method as in Comparative Example 5. The complex was evaluated according to the evaluating method as mentioned in the above <Evaluation of Adhesion Preventing Materials> and, when an observation was done by means of an incision after 8 weeks, the degradation rate of the complex was slow inhibiting the repair of the tissue.

EFFECT OF THE INVENTION

The biomaterial prepared by the present invention comprising calcium phosphate and a copolymer of lactic acid, glycolic acid and ε-caprolactone shows an excellent biocompatibility, appropriate strength and degradation rate and is a material which is effective for the regeneration of tissues. When the biomaterial is used as a reconstructing material for hard tissues or soft tissues, its strength is retained during the period until the tissues are regenerated and it is absorbed into the organism together with the regeneration of the tissues whereby it does not inhibit the regeneration of the tissues. In addition, there is no foreign body reaction by the residue.

Further, the biomaterial for inducing the osteoanagenesis where periosteum is attached to a complex containing calcium phosphate and a copolymer of lactic acid, glycolic acid and ε-caprolactone prepared by the present invention has an excellent biocompatibility, appropriate rigidity and degradation rate and can be freely adjusted depending upon the shape of the site to be treated. The said complex is gradually degraded in vivo whereupon calcium phosphate is released therefrom. During the osteoanagenetic stage, the material functions as a partition between the site to be treated and the outer area, inhibits the invasion of fibroblasts from the surrounding soft tissues and forms an environment which is advantageous for the osteoanagenesis. At the same time, hematopoietic cells are provided from the periosteum while calcium phosphate is provided from the said complex to promote the osteoanagenesis and, after the osteoanagenesis, the material is metabolized or becomes a part of the bone in vivo. Accordingly, the material can be used for the therapy of big bone defect part for which a complete therapy has not been possible in the conventional methods and the material can be effectively used for a regenerative therapy of bone tissues.

Furthermore, the biomaterial for the prevention of adhesion in accordance with the present invention is in such a structure that calcium phosphate is coordinated to a carbonyl group in the copolymer of lactic acid, glycolic acid and ε-caprolactone and, therefore, the acid which is produced as a result of degradation of the copolymer is neutralized by a degradation of calcium phosphate in vivo whereby the strength of the material can be retained. Accordingly, the biomaterial shows a neutral characteristic in vivo and, therefore, damage of the biotissues is very little. In addition, the biomaterial shows a very high strength and, therefore, it is suitable as a material for the prevention of adhesion.

For example, when the copolymer used in the present invention having a film thickness of 300 μm is solely dipped in a physiological saline of 37° C. for 4 weeks, pH of the solution is 3–4 while, in the case of the material for the prevention of adhesion in accordance with the present invention, a neutral pH of 6.5–7 is retained. Further, with regard to its tensile strength, the necessary strength lowers within 2 weeks in the former case of the copolymer only while, in the material of the present invention, its strength can be retained for 12 weeks or even longer.

Accordingly, the material for the prevention of adhesion in accordance with the present invention does not inhibit the repair of the biotissues and has a degradation rate which is suitable for the adhesion of the applied site.

Although the shape of biotissues are complicated in general, it is possible to manufacture various types of materials ranging from flexible to highly strong ones by adjusting the composition and the molecular weight of the copolymer of lactic acid, glycolic acid and ε-caprolactone. Therefore, the material of the present invention for the prevention of adhesion is not broken by compression of the tissues and can be fixed to the tissues in a closely contact manner achieving an excellent effect of prevention of adhesion.

Thus, when the biomaterial of the present invention for the prevention of adhesion is used in vivo, its strength is retained during the period until the tissues are repaired and it is gradually absorbed into the organism together with the repair of the tissues whereby it is a material for the prevention of adhesion which is applicable to a broad site.

The biomaterial of the present invention for the prevention of adhesion shows an excellent biocompatibility and has appropriate strength and degradation rate and, therefore, it has an excellent tissue repairing ability. During the period until the tissue is repaired, its shape and strength are retained and it is absorbed into an organism together with the repair of the tissue whereby it is an excellent material where the tissues do not adhere to each other and there is no residue which causes the foreign body reaction.

What is claimed is:

1. A biomaterial comprising calcium phosphate and a copolymer of lactic acid, glycolic acid and ε-caprolactone, wherein the ε-caprolactone content in the copolymer is within a range of about 1 to abut 45 molar % and the glycolic acid content in the copolymer is within a range of about 5 to about 70 molar %.

2. The biomaterial according to claim 1, which is a biomaterial for the induction of osteoanagenesis or a biomaterial for the prevention of adhesion.

3. A biomaterial for the induction of osteoanagenesis, characterized in that a periosteum is attached to the biomaterial comprising calcium phosphate and a copolymer of lactic acid, glycolic acid and ε-caprolactone.

4. The biomaterial for the induction of osteoanagenesis according to claim 3, characterized in that a periosteum is attached by means of a suture and an adhesion to the biomaterial.

5. The biomaterial for the induction of osteoanagenesis according to claim 3, whose rigidity is 200–20000 MPa at 4–40° C.

6. The biomaterial for the induction of osteoanagenesis according to claim 3, characterized in that the copolymer has a molar ratio of lactic acid, glycolic acid and ε-caprolactone within a range of 5–90:3–75:5–40 in the biomaterial.

7. A biomaterial for the prevention of adhesion comprising calcium phosphate and a copolymer of lactic acid, glycolic acid and ε-caprolactone where the molar ratio of lactic acid, glycolic acid and ε-caprolactone is within a range of 5–90:3–75:5–40.

8. The biomaterial according to claim 1, wherein a ratio of calcium phosphate to the copolymer in terms of weight is 1:0.1~2.0.

9. The biomaterial according to claim 1, which is manufactured by heating and kneading calcium phosphate with the copolymer.

10. The biomaterial according to claim 9, wherein the heating/kneading temperature is 50–250° C.

11. The biomaterial according to claim 1, wherein the number-average molecular weight of the copolymer is 30,000–200,000.

12. The biomaterial according to claim 1, wherein calcium phosphate is tricalcium phosphate.

13. The biomaterial according to claim 12, wherein tricalcium phosphate has a particle size of 0.1 to 200 μm.

14. The biomaterial according to claim 12, wherein tricalcium phosphate is sintered at 650–1500° C.

* * * * *

UNITED STATES PATENT AND TRADEMARK OFFICE
CERTIFICATE OF CORRECTION

PATENT NO. : 6,441,073 B1
DATED : August 27, 2002
INVENTOR(S) : Tanaka et al.

It is certified that error appears in the above-identified patent and that said Letters Patent is hereby corrected as shown below:

<u>Title page,</u>
Item [75], Inventors, "Shunji Ichikawa," should be spelled -- Toshiji Ichikawa --
Item [73], Assignees, " National Institute for Material Science President," should be spelled -- National Institute for Materials Science President -- and -- KAWASUMI LABORATORIES, INC. -- should be added as an assignee Signed and Sealed this Twenty-first Day of January, 2003

JAMES E. ROGAN
*Director of the United States Patent and Trademark Office*